(12) United States Patent
St. George et al.

(10) Patent No.: US 10,011,895 B2
(45) Date of Patent: Jul. 3, 2018

(54) ASSEMBLY FABRICATION AND MODIFICATION OF ELASTICITY IN MATERIALS

(71) Applicant: Gyrus Acmi, Inc., Southborough, MA (US)

(72) Inventors: Lawrence J. St. George, Sudbury, MA (US); Gregory Konstorum, Stamford, CT (US); Antonio E. Prats, Shrewsbury, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 591 days.

(21) Appl. No.: 14/687,176

(22) Filed: Apr. 15, 2015

(65) Prior Publication Data

US 2015/0320390 A1 Nov. 12, 2015

Related U.S. Application Data

(60) Provisional application No. 61/989,173, filed on May 6, 2014.

(51) Int. Cl.
| | | |
|---|---|---|
| *C22C 14/00* | (2006.01) | |
| *C22F 1/18* | (2006.01) | |
| *A61B 8/00* | (2006.01) | |
| *G01N 29/22* | (2006.01) | |
| *G10K 11/24* | (2006.01) | |
| *B06B 3/00* | (2006.01) | |

(52) U.S. Cl.
CPC .............. *C22F 1/18* (2013.01); *A61B 8/4444* (2013.01); *B06B 3/00* (2013.01); *C22C 14/00* (2013.01); *C22F 1/183* (2013.01); *G01N 29/221* (2013.01); *G10K 11/24* (2013.01)

(58) Field of Classification Search
CPC ...................................................... C22C 14/00
See application file for complete search history.

(56) References Cited

U.S. PATENT DOCUMENTS

| | | |
|---|---|---|
| 5,141,566 A | 8/1992 | Kitayama et al. |
| 5,600,989 A | 2/1997 | Segal et al. |
| 6,197,129 B1 | 3/2001 | Zhu et al. |
| 6,209,379 B1 | 4/2001 | Nishida et al. |
| 6,399,215 B1 | 6/2002 | Zhu et al. |
| 6,569,270 B2 | 5/2003 | Segal |
| 7,148,772 B2 | 12/2006 | Sherrer et al. |
| 7,405,638 B2 | 7/2008 | Sherrer et al. |
| 8,506,201 B2 | 8/2013 | Slattery |
| 8,613,818 B2 | 12/2013 | Forbes Jones et al. |
| 2002/0153071 A1 | 10/2002 | Segal et al. |
| 2005/0145310 A1 | 7/2005 | Bewlay et al. |

(Continued)

FOREIGN PATENT DOCUMENTS

WO 2009079651 A2 6/2009

*Primary Examiner* — Jessee Roe
(74) *Attorney, Agent, or Firm* — Chapin IP Law, LLC (57) ABSTRACT

A fabricator resource receives an assembly including a first portion of material and a second portion of material. Initially, the first portion of material in the assembly may have a different modulus of elasticity than the second portion of material. The fabricator resource exposes the assembly to one or more heating/cooling cycles. Exposure of the assembly to the one or more heating/cooling cycles modifies a modulus of elasticity of the first portion of material and a modulus of elasticity of the second portion of material to desired target values (such as substantially same or different values).

9 Claims, 10 Drawing Sheets

(56) References Cited

U.S. PATENT DOCUMENTS

| | | |
|---|---|---|
| 2007/0193018 A1 | 8/2007 | Davis et al. |
| 2009/0058569 A1 | 3/2009 | Sherrer et al. |
| 2011/0210807 A1 | 9/2011 | Sherrer et al. |
| 2013/0253387 A1 | 9/2013 | Bonutti et al. |

ASSEMBLY FABRICATION AND MODIFICATION OF ELASTICITY IN MATERIALS

RELATED APPLICATIONS

This application is related to and claims the benefit of earlier filed U.S. Provisional Patent Application Ser. No. 61/989,173 entitled "ASSEMBLY FABRICATION AND MODIFICATION OF ELASTICITY IN MATERIALS," filed on May 6, 2014, the entire teachings of which are incorporated herein by this reference.

BACKGROUND

Titanium is used in many applications due to its relatively low weight and strengthening properties. For example, titanium can be mixed with one or more other metals to produce different types of titanium metal alloys. Such titanium alloys are widely used in different types of applications because of their good combinations of strength, toughness, and formability.

Atoms of pure titanium align in the solid state in either a hexagonal close-packed crystalline structure, called the alpha ($\alpha$) phase, or a body-centered cubic structure, called the beta ($\beta$) phase. In a pure metal, transformation from the alpha to the beta phase occurs upon heating above a temperature such as 883° C. Most alloying elements either stabilize the alpha phase to higher temperatures or stabilize the beta phase to lower temperatures. For example, Aluminum (Al) and oxygen are typical alpha-stabilizing elements, and typical beta-stabilizing elements are vanadium (V), iron (Fe), molybdenum (Mo), nickel (Ni), palladium (Pd), niobium (Nb), silicon (Si), and chromium (Cr). A few other alloying elements, such as tin (Sn) and zirconium (Zr), have little effect on phase stabilization.

The lowest temperature at which a 100-percent beta phase can exist is called the beta transus; this can range from 700° C. (1,300° F.) to as high as 1,050° C. (1,900° F.), depending on alloy composition. Final mechanical working and heat treatments of titanium alloys are generally conducted below the beta transus temperature in order to achieve the proper microstructural phase distribution.

BRIEF DESCRIPTION

Conventional techniques of producing a titanium alloy component or assembly having precise physical characteristics suffer from deficiencies. For example, an ultrasonic probe assembly such as a titanium probe may require that the corresponding titanium alloy used to produce the titanium probe has a Young's modulus of elasticity that is a very specific value and is substantially the same along its length. Young's modulus, also known as the tensile modulus or elastic modulus, is a measure of the stiffness of an elastic isotropic material and is a quantity used to characterize materials. It is defined as the ratio of the stress along an axis over the strain along that axis in the range of stress in which Hooke's law holds.

A variation in the modulus of elasticity (or Young's modulus) along the length of the probe (if the elasticity is outside a desired tolerance) reduces the usefulness of the probe because portions of material outside the desired elasticity range dampen a respective ultrasonic signal conveyed from one end of the probe to the other.

One way to fabricate a respective titanium probe (such as one that varies in diameter along its length) is to receive a sufficiently large mass such as a rod or block of homogeneous titanium alloy material having a substantially same Young's modulus value throughout. A fabricator resource machines off an unwanted portion of the original mass of titanium alloy material to produce an assembly having a desired form. Assuming that the initial large mass of titanium alloy material had appropriate desired characteristics (such as a homogeneous modulus of elasticity throughout the material), and that the process of machining did not change these characteristics of the material, the resulting titanium probe formed by machining (removal of unwanted material) results in a titanium probe tuned to convey ultrasonic signals in a desired frequency range.

This disclosure includes the observation that titanium alloy material is expensive and that, depending on a final shape of the probe, as much as or more than 80% of material in an original mass of titanium alloy material may need to be removed to produce a titanium probe having desired characteristics. The machined-off material is typically not very valuable. Because substantial machining is needed, it can be difficult to easily and reliably, produce a titanium probe that exhibits the necessary precise physical characteristics required for proper performance in a respective ultrasonic system.

In contrast to conventional techniques, embodiments herein include a first fabricator resource that receives a first portion of material and a second portion of material. By way of non-limiting example, assume that the first portion of material and the second portion of material are of approximately the same titanium alloys. The first fabricator resource joins (via a suitable process such as welding, forging, molding, casting, etc.) the first portion of material and second portion of material to form an assembly such as a probe or other suitable device.

In accordance with further embodiments, a second fabricator resource receives the assembly including the first portion of material and a second portion of material. Assume in this example that the first portion of material initially has a different modulus of elasticity than the second portion of material in the assembly. In one embodiment, the second fabricator resource exposes the assembly to a first heating/cooling cycle in which the assembly is exposed to a temperature greater than a beta transus temperature associated with the material in the assembly (probe in this example). In one embodiment, exposure of the assembly to the first heating/cooling cycle resets a modulus of elasticity of the first portion of material and a modulus of elasticity of the second portion of material to be a substantially same modulus of elasticity value (reset elasticity value).

Subsequent to resetting the modulus of elasticity value of the first portion of material and the second portion of material in the assembly, the second fabricator resource anneals the assembly to change the modulus of elasticity of the assembly to a desired target value above (or possibly below) the reset elasticity value. For example, in one embodiment, the second fabricator resource exposes the assembly (and corresponding first portion of material and second portion of material) to one or more additional heating/cooling cycles to set the modulus of elasticity of the material in the assembly to a desired target value within a predetermined range. The one or more additional heating/cooling cycles can include exposing the assembly to a temperature such as between 300 and 900 degrees Celsius and then cooling back to room temperature.

In certain instances, the annealing process may require exposing the assembly to additional heating/cooling cycles in order to change the modulus of elasticity of the material to a desired target value.

In one embodiment, modifying the material in the assembly to be within a desired elasticity range tunes the titanium alloy assembly to support conveyance of ultrasonic frequencies in a desired range along an axial length from a proximal end of the assembly through the first portion of material and the second portion of material to a distal end of the assembly.

Embodiments herein are beneficial over conventional techniques. For example, as previously discussed, conventional methods of machining off a large amount of expensive material to produce an assembly (such as a probe or other suitable shape) of a desired shape and having a substantially homogenous modulus of elasticity is undesirable. In contrast to conventional techniques, embodiments herein include controlling characteristics of material in a respective assembly via exposure to one or more heating/cooling cycles, reducing an amount of wasted material, as well as machining and energy resources used, yet producing an assembly having desired characteristics.

These and other embodiment variations are discussed in more detail below.

Note that embodiments herein can include a configuration of one or more computerized devices, hardware processor devices, assemblers, fabricator resources, or the like to carry out and/or support any or all of the method operations disclosed herein. In other words, one or more computerized devices, processors, digital signal processors, assemblers, etc., can be programmed and/or configured to perform the method as discussed herein.

Additionally, although each of the different features, techniques, configurations, etc., herein may be discussed in different places of this disclosure, it is intended that each of the concepts can be executed independently of each other or in combination with each other. Accordingly, the one or more present inventions, embodiments, etc., as described herein can be embodied and viewed in many different ways.

Also, note that this preliminary discussion of embodiments herein does not specify every embodiment and/or incrementally novel aspect of the present disclosure or claimed invention(s). Instead, this brief description only presents general embodiments and corresponding points of novelty over conventional techniques. For additional details and/or possible perspectives (permutations) of the invention(s), the reader is directed to the Detailed Description section and corresponding figures of the present disclosure as further discussed below.

The foregoing and other objects, features, and advantages of the invention will be apparent from the following more particular description of preferred embodiments herein, as illustrated in the accompanying drawings in which like reference characters refer to the same parts throughout the different views. The drawings are not necessarily to scale, with emphasis instead being placed upon illustrating the embodiments, principles, concepts, etc.

DETAILED DESCRIPTION AND FURTHER SUMMARY OF EMBODIMENTS

In general, as described herein, a fabricator resource receives an ultrasonic probe assembly including a first portion of material and a second portion of material. Initially, the first portion of material in the assembly may have a different modulus of elasticity than the second portion of material. The fabricator resource exposes the assembly to one or more heating/cooling cycles. Exposure of the assembly and corresponding portions of material to the one or more heating/cooling cycles modifies a modulus of elasticity (such as Young's modulus) of the first portion of material and a modulus of elasticity of the second portion of material to one or more desired target values.

As described herein, certain embodiments herein include setting the modulus of elasticity of the material in the assembly to a homogenous value. Alternative embodiments herein include setting the modulus of elasticity of the material in the assembly to heterogeneous values such that different portions of the assembly have different Young's modulus values.

In one embodiment, an assembly may be fabricated from different portions of material of substantially the same alloy. However, initially, although the material is of the same type of alloy, each of the different portions of material may have different Young's modulus characteristics. Embodiments herein include exposing the respective assembly to one or more heating/cooling cycles to modify settings of the material in the assembly. Controlling the setting of material in the assembly to be a substantially same Young's modulus value controls a resonant frequency of the corresponding assembly. For example, assume that the material in the assembly is a titanium alloy such as Ti6Al4V. In one non-limiting example embodiment, controlling the characteristics of material in a respective probe assembly to be a Young's modulus target range value of $E=107.0\pm3.0$ Giga Pascals (GPa) tunes the respective assembly to support an optimum acoustic transmission frequency of $50\pm3.5$ KiloHertz (KHz). Note that these settings are shown by way of non-limiting example only and that desired attributes of a respective assembly can be adjusted depending on the application. As further discussed below, characteristics of an assembly can be more tightly controlled within narrower or different ranges if desired.

Figure 1:
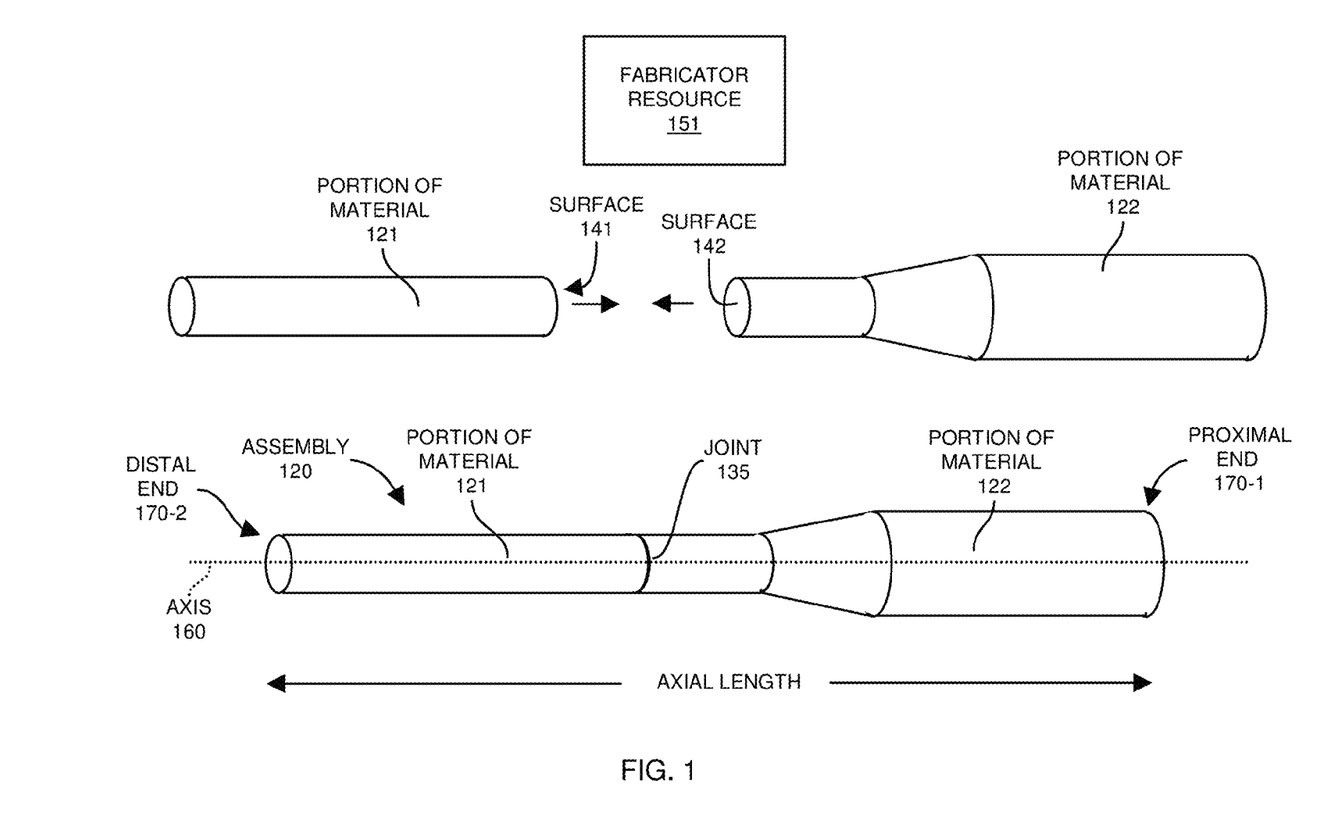
FIG. 1 is an example diagram of a fabricator resource configured to produce an assembly according to embodiments herein.

Now, more specifically, FIG. 1 is an example diagram of a fabricator resource configured to produce an assembly according to embodiments herein.

As shown, fabricator resource 151 receives a portion of material 121 and portion of material 122. The first portion of material 120 and second portion of material 122 can be any suitable shape or size. For example, in one non-limiting example embodiment, the first portion of material 121 is approximately ⅛ inch in diameter and is between one and twenty inches long; the second portion of material 122 is approximately ¼ inch in diameter and is between one and four inches long.

In accordance with further embodiments, both the first portion of material 121 and second portion of material 122 are of a substantially the same composite of titanium alloy such as Ti6Al4V. If desired, the titanium alloy Ti6Al4V from which the portions of material are fabricated can conform to any suitable standard such as JIS (Japanese Industrial Standards) H4650-TAB6400H, standard ASTM B348 GR5, etc.

In accordance with further embodiments, assume that the first portion of material 121 and the second portion of material 122 are fabricated from Titanium alloy(s) having a substantially same alloy composition, grain size, alpha/beta ratio, etc., although these parameters may vary from one portion to another.

Even though the first portion of material 121 and the second portion of material 122 are of a substantially same composite material, the first portion material 121 may have a first Young's modulus setting; the second portion material 122 may have a second Young's modulus setting which is different than the first Young's modulus setting. In other words, an elasticity of the material of the assembly 120 can vary along the length.

In one embodiment, if desired, X-ray fluorescence or other suitable measurement techniques can be used to accurately measure the constituents (or components) of the alloy mixture of the different portions of material 121, 122, etc., that are used to fabricate assembly 120. In certain instances, a respective manufacturer providing the raw material (from which the first portion of material 121 and second portion of material 122 is fabricated) provides information indicating a composition of the raw material and any other useful specifications.

As further shown in FIG. 1, the fabricator resource 151 fixedly attaches (joins) surface 141 of the portion of material 121 and surface 142 of the portion of material 122 via a corresponding joint 135 to produce assembly 120 such as a probe.

Note that the fabricator resource 151 can produce joint 135 in any suitable manner. In one embodiment, the fabricator resource 151 produces the joints 135 via friction welding. In accordance with another embodiment, the fabricator resource 151 produces the joint 135 via investment casting. In accordance with yet another embodiment, the fabricator resource 151 produces the joint 135 via molding in which two solid rods (such as first portion of material 121 and second portion material 122) are heated in a containing mold. In still another embodiment, the fabricator resource 151 can be configured to produce the joint 135 via forging, in which surface 141 of the first portion material 121 and surface 142 of the second portion of material 122 forming respective joint 135 are heated (such as via contacting surfaces 141 and 142 and spinning one portion of material about axis 160 with respect to the other) and pushed together as shown.

Note that the proximal end 170-1 (such as a base) and distal end 170-2 (such as a tip) of assembly 120 can be formed to be any suitable shape depending upon the application. In one embodiment, the assembly 120 is part of a probe used in the Thunderbeat™ product developed by Olympus™.

In one instance, it is desired that the assembly 120 supports ultrasonic transmission of signals along the axis 160 of assembly from the proximal end 170-1 to the distal end 170-2 in a frequency range of 50±3.25 KiloHertz (KHz), although this may vary depending on the embodiment.

As previously discussed, each of the portions of material 121 and 122 may have a different Young's modulus setting. As further discussed below, creation of joint 135 (based on heat treating) may alter corresponding characteristic of material in vicinity of joint 135, resulting in yet another variation in characteristic (such as a Young's modulus setting) of the assembly 120 from the proximal end 170-1 to the distal end 170-2.

Figure 2:
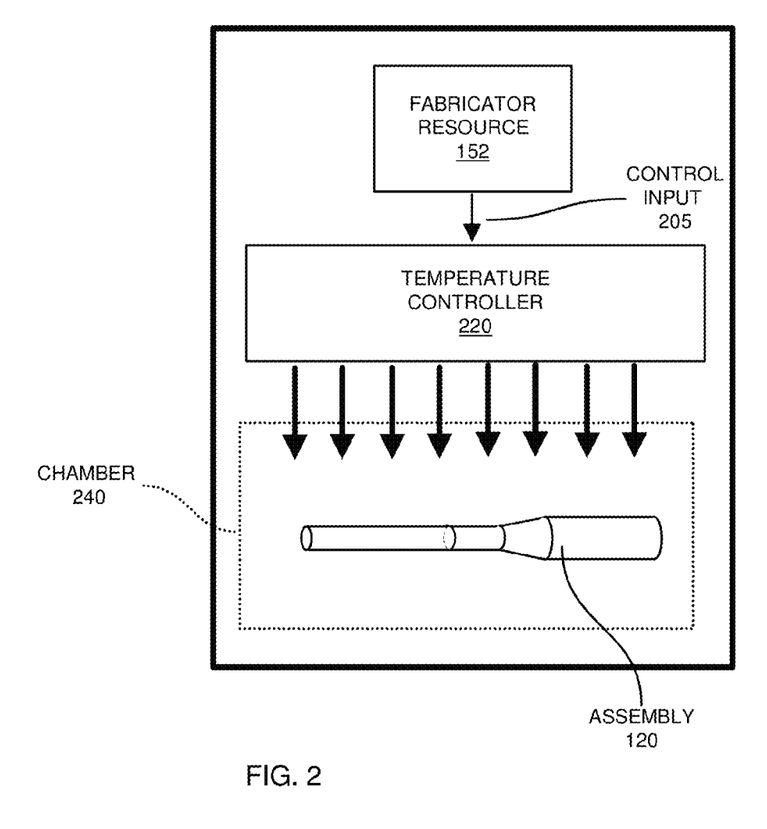
FIG. 2 is an example diagram illustrating exposure of an assembly to one or more heating/cooling cycles according to embodiments herein.

FIG. 2 is an example diagram illustrating exposure of an assembly to one or more heating/cooling cycles according to embodiments herein.

As shown, fabricator resource 152 provides control input 205 to temperature controller 220. In accordance with control input 205, temperature controller 220 controls the temperature of chamber 240 in which assembly 120 resides.

In one embodiment, the temperature controller 220 is able to control the chamber 240 to any suitable temperature value as specified by control input 205 such as greater than 1000° C. or less than 50° C.

As further discussed below, if desired, as specified by control input 205, temperature controller 220 is able to quickly increase or decrease the temperature of chamber 240 and/or its contents (such as assembly 120 such as an ultrasonic probe assembly) to modify attributes (such as a Young's modulus of elasticity) of assembly 120.

Figure 3A:
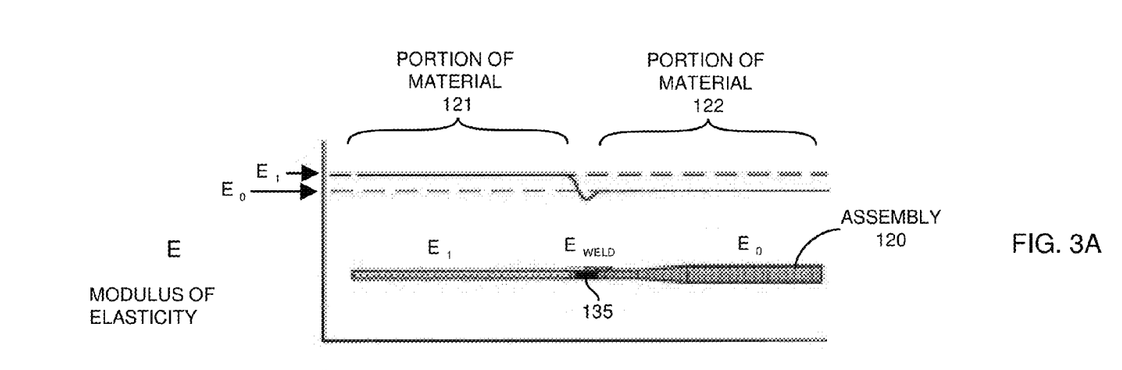
FIGS. 3A, 3B, and 3C are example diagrams illustrating modification of a modulus of elasticity of material in an assembly via exposure of the assembly to one or more heating/cooling cycles according to embodiments herein.

FIG. 3A is an example graph illustrating initial Young's modulus settings of assembly along its length according to embodiments herein.

As shown, the first portion material 121 of assembly 120 has a Young's modulus setting of E1; second portion material 122 in assembly 120 has a Young's modulus setting of E0; joint 135 of assembly 120 has a Young's modulus setting of Eweld. The heat caused by joining portion of materials causes the Young's modulus of the joint to be different than adjacent material in the first portion of material 121 and second portion of material 122.

As previously discussed, one embodiment herein includes modifying values of the Young's modulus setting along the length of the assembly 120 to a substantially homogeneous value. Other embodiments as further discussed below in FIGS. 9 and 10 include producing an assembly that has a varying Young's modulus (elasticity) along its length.

Figure 3B:
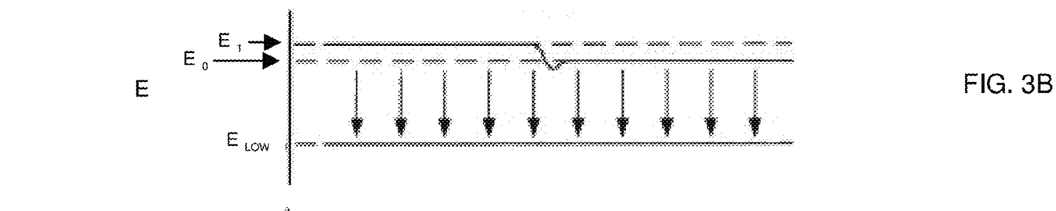

FIG. 3B is an example graph illustrating application of a heating/cooling cycle to the assembly to reset the Young's modulus to a reset value according to embodiments herein.

In one embodiment, the fabricator resource 152 transmits control input 205 to temperature controller 220 to, in turn, control the temperature of assembly 120 in chamber 240 to above a beta transus temperature value such as above 1000+/−15° C. for an appropriate duration of time (e.g., a suitable time such as more than 30 minutes). It is known that pure titanium has two solid crystalline forms. At relatively low temperatures, the crystalline phase is called alpha, and it has a hexagonal closed packed (HCP) structure. At high temperatures, the solid phase is called beta and has a body centered cubic (BCC) structure. The temperature at which the solid becomes fully beta is called the beta-transus temperature.

After heating the assembly 120 for the appropriate amount of time as specified by control input 205, the fabricator resource 152 initiates quench cooling of the assembly 120. As previously discussed, quench cooling can include exposing the assembly 120 to a liquid (such as water, oil, etc.) below a temperature of 100 degrees Celsius. By way of non-limiting example embodiment, the fabricator resource 152 can be configured to cool assembly 120 from a temperature of over 1000° C. to less than 50° C. in less than several seconds. After cooling, as shown in FIG. 3B, the material in assembly 120 is reset to the homogeneous Young's modulus value of Elow.

Figure 3C:
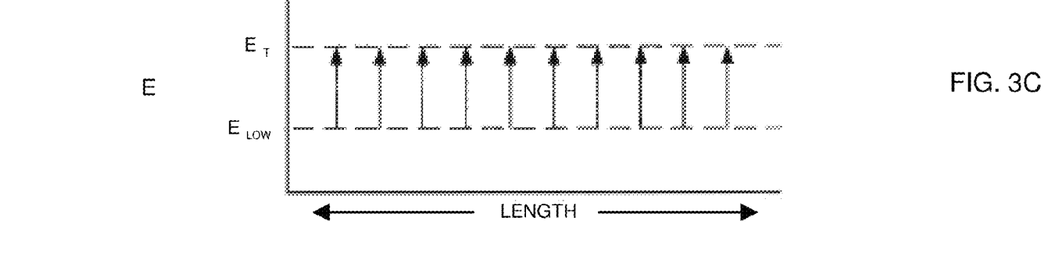

FIG. 3C is an example graph illustrating application of one or more subsequent heating/cooling cycles to the assembly to tune the assembly to a desired resonance frequency according to embodiments herein.

Figure 5:
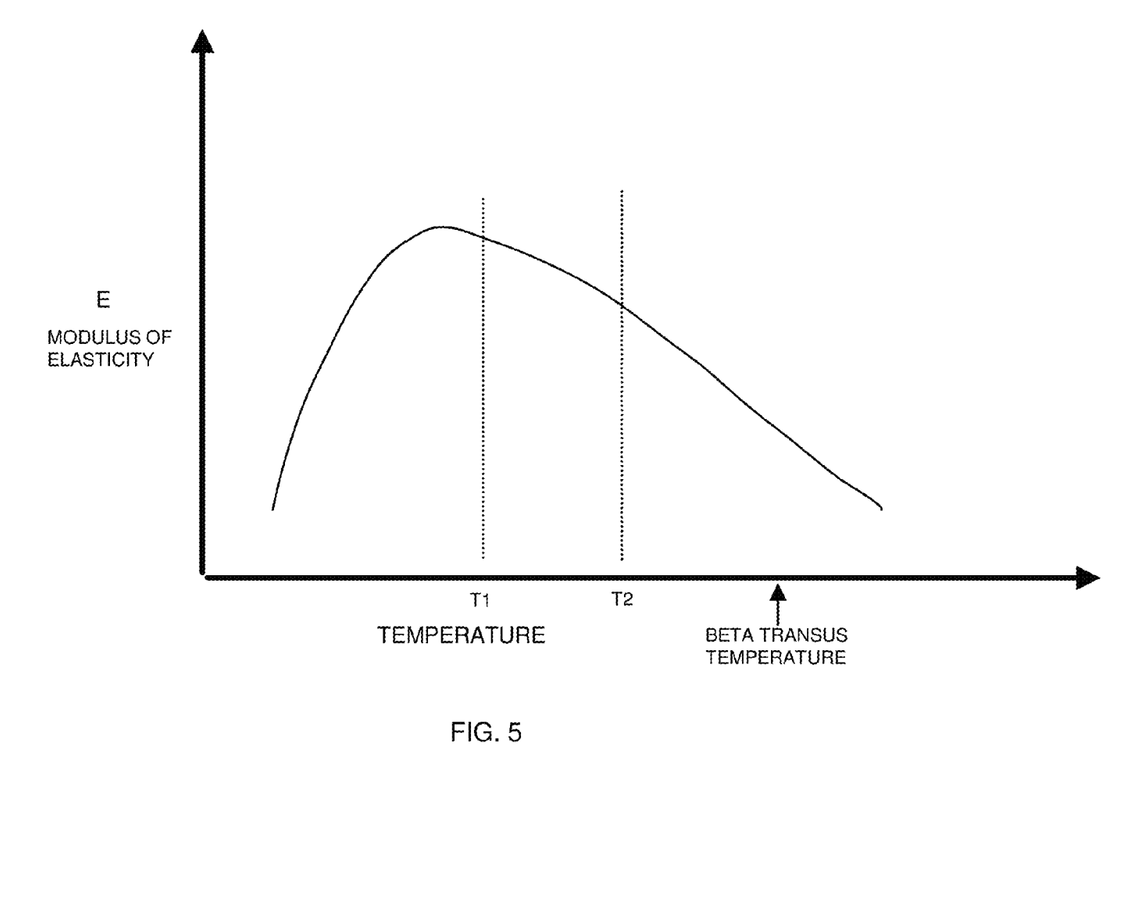
FIG. 5 is an example diagram illustrating a graph of a modulus of elasticity versus temperature for a titanium alloy.

In this example embodiment, the fabricator resource 152 controls application of one or more heating/cooling cycles to carefully anneal the material in the assembly 120. In one embodiment, the fabricator resource 152 controls the temperature of assembly 120 in chamber 240 to be in a range between T1 (such as 300° C.) and T2 (such as 900° C.) for a predetermined duration of time. FIG. 5 is an example diagram illustrating a graph of Young's modulus of elasticity versus temperature and corresponding temperature range between T1 and T2.

After the fabricator resource 152 controls the temperature of assembly 120 to be greater than 300 and less than 900 degrees for a duration such as more than 30 minutes to modify the elasticity setting of material in assembly 120, the fabricator resource 152 reduces the temperature in chamber 240 to reduce the temperature of assembly 120 to below 50° C. In one embodiment, the fabricator resource 152 ramps down the temperature of assembly 120 from a starting value within the range (between 300 and 900 degree Celsius) to room temperature of about 20° C. over a several minute time span. In other words, the assembly can be slowly cooled. This causes the material along a length of assembly 120 to be set to a homogeneous Young's modulus value of Et as further shown in FIG. 3C.

In certain instances, note that it may be required to expose the assembly 120 to multiple heating/cooling cycles in order to raise the setting of the Young's modulus from Elow to a value (such as Et) within a desired target range.

In one embodiment, a determination of environmental control parameters (such as temperature, duration of exposure to temperature, . . . ) associated with the heating and cooling cycles that are needed to modify an assembly such that its Young's modulus fall within a desired range is determined based on trial and error.

For example, embodiments herein can include applying a temperature in a range between 300 and 900° C. for a certain duration of time and then determining a Young's modulus setting resulting from the previously applied heating/cooling cycle. If the resulting Young's modulus setting of the respective assembly 120 after exposing the assembly 120 to a first heating/cooling cycle is not within a desired range, the fabricator resource 152 can be configured to expose the assembly 120 to one or more additional heating/cooling cycles until the assembly 120 has a homogeneous Young's modulus setting within the desired range. The duration or temperature can be modified each successive time of applying a heating/cooling cycle so that the characteristic of assembly 120 are closer to a desired target value.

After application of a respective heating/cooling cycle, any suitable method can be used to determine modulus of elasticity settings associated with assembly 120. For example, embodiments herein can include implementing acoustic scanning, ultrasonic scanning, optical scanning, laser scanning, thermal scanning, x-ray scanning, x-ray fluorescence scanning, pull testing, etc., of the assembly 120 to determine whether characteristic (such as its elasticity) of the assembly 120 conforms to desired settings.

As previously discussed, the composition of the one or more alloy materials used to fabricate the assembly 120 may be known. After learning of one or more appropriate heating/cooling cycles that are needed to modify different possible compositions of titanium alloy material via trial and error, the fabricator resource 152 can be configured to determine attributes of an next assembly and then implement an appropriate one or more learned heating/cooling cycles techniques (from previous trial and error) to apply and modify the material in a newly received assembly such that the Young's modulus of the material in the new assembly modified to be within a desired range.

As previously discussed, one embodiment herein includes applying one or more subsequent heating/cooling cycles to modify the Young's modulus setting along the length of the assembly 120 such that a Young's modulus of the assembly 120 is a substantially homogeneous value within a desired target range such as E=103.0 GigaPascals to 110.0 GigaPascals, preferably 104.0 GigaPascals to 109.0 GigaPascals, and most preferably 105.0 GigaPascals to 108.0 Gigapascals. If desired, the Young's modulus setting along the length can be controlled to a more narrow range of E=104.0–GigaPascals to 109.0 GigaPascals, preferably 105.0 GigaPascals to 108.0 GigaPascals, and most preferably 106.0 GigaPascals to 107.0 GigaPascals to support translation of acoustics signals along the axial length of assembly 120 at a resonance frequency of 50±3.5 KiloHertz (KHz).

In contrast to conventional techniques in which fabricators desire to produce titanium alloy material that does not resonate (to prevent self-destruction of a respective component), embodiments herein include tuning the assembly 120 to resonate within a desired frequency range when exposed to a respective ultrasonic excitation frequency signal.

Figure 4:
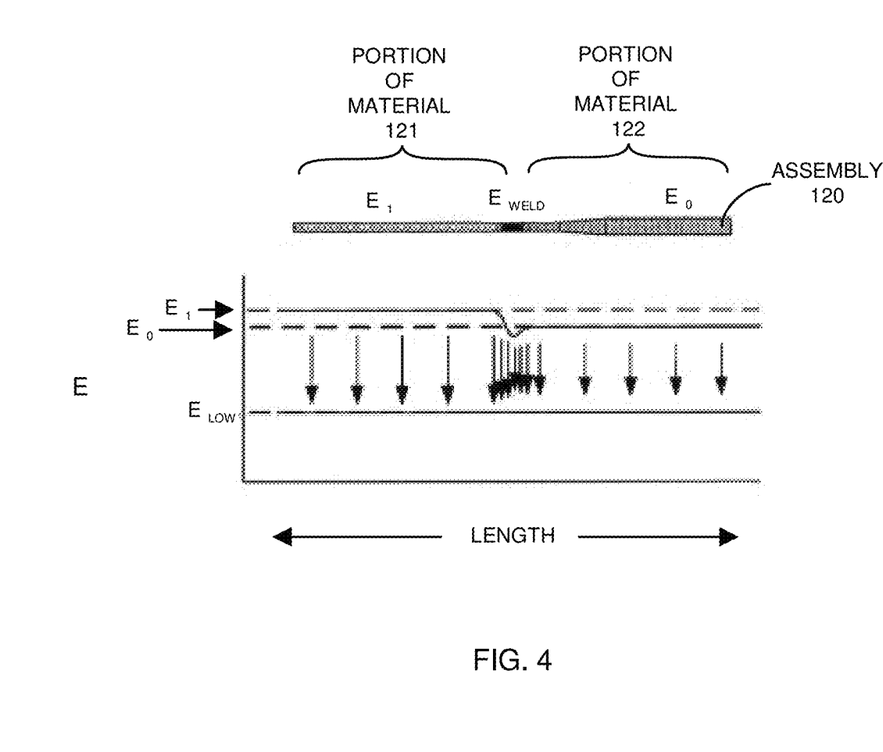
FIG. 4 is an example diagram illustrating an alternative method (to FIG. 3B) of applying heat to reset a modulus of elasticity of an assembly according to embodiments herein.

FIG. 4 is an example diagram illustrating an alternative method (to FIG. 3B) of applying heat to reset a modulus of elasticity of an assembly to a desired reset value according to embodiments herein.

In this example embodiment, in contrast to FIG. 3B, the fabricator resource 152 applies different amounts of heat (e.g., heat at different temperatures) along a length of the assembly 120 to reset the Young's modulus of the assembly 120 to a homogenous reset value of Elow. In a similar manner as previously discussed with respect to FIG. 3C, after resetting the value to Elow, the fabricator resource 152 then anneals the material (as in Fabricator 3C) in assembly 120 to adjust the homogenous Young's modulus of elasticity and tune the assembly 120 within a desired resonance frequency range.

Figure 6:
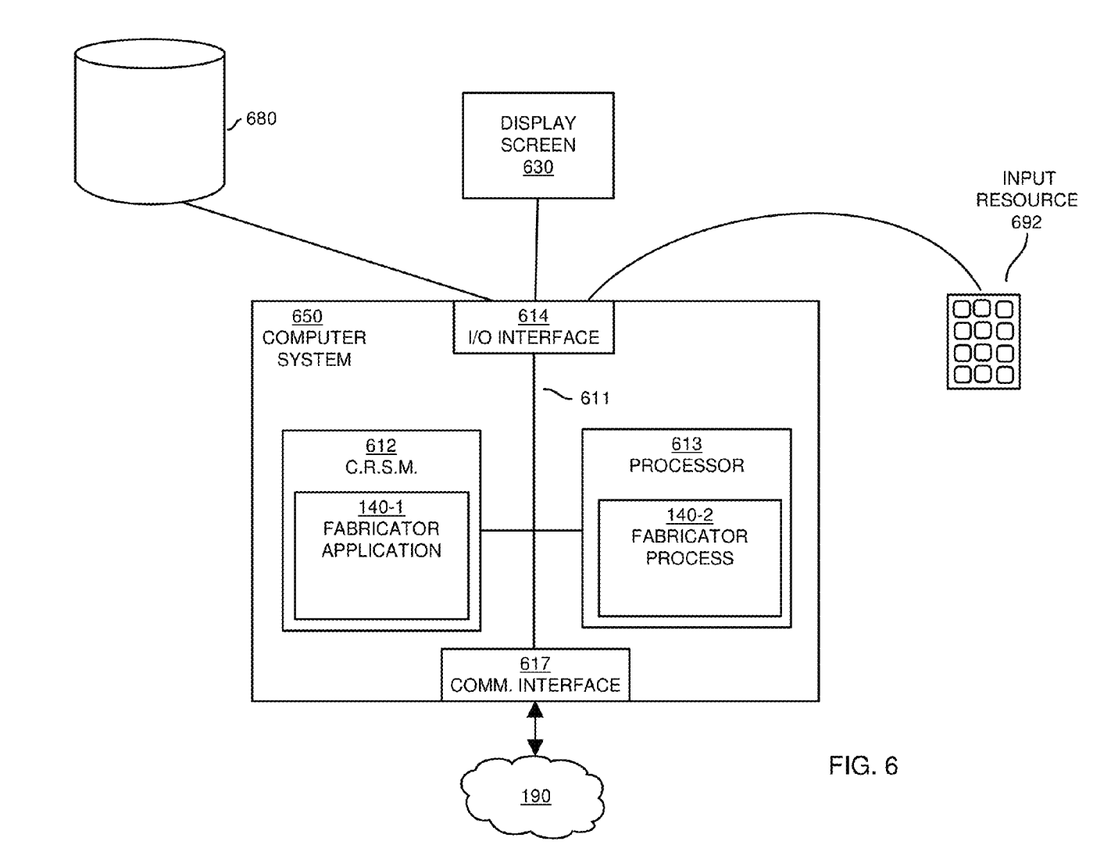
FIG. 6 is an example diagram illustrating a computer system (such as a fabricator resource) executing one or more instructions to modify characteristics of an assembly according to embodiments herein.

FIG. 6 is an example diagram illustrating a computer system (such as located in a fabricator resource 151, 152, etc.) executing one or more instructions to modify characteristics of an assembly according to embodiments herein. Any of the different processing techniques to fabricate an assembly 120 having desired characteristics can be achieved via execution of software code on computer processor hardware.

As shown, computer system 650 (e.g., computer processor hardware) of the present example can include an interconnect 611 that couples computer readable storage media 612 such as a non-transitory type of media (i.e., any type of hardware storage medium) in which digital information can be stored and retrieved. The computer system 650 can further include processor 613 (i.e., computer processor hardware such as one or more processor co-located or disparately located processor devices), I/O interface 614, communications interface 617, etc.

Computer processor hardware (i.e., processor 613) can be located in a single location or can represent multiple resources to be distributed amongst multiple locations in a fabrication environment.

As its name suggests, I/O interface 614 provides connectivity to resources such as repository 680, control devices (such as controller 692), one or more display screens 630, etc.

Computer readable storage medium 612 can be any hardware storage device to store data such as memory, optical storage, hard drive, floppy disk, etc. In one embodiment, the computer readable storage medium 612 stores instructions and/or data.

Communications interface 617 enables the computer system 650 and processor resource 613 to communicate over a resource such as a network 190. I/O interface 614 enables processor resource 613 to access data from a local or remote location, control a respective display screen, receive input, etc.

As shown, computer readable storage media 612 can be encoded with fabricator application 140-1 (e.g., software, firmware, etc.) executed by processor 613 (computer processor hardware). Fabricator application 140-1 can be configured to include instructions to implement any of the processing operations as discussed herein.

During operation of one embodiment, processor 613 accesses computer readable storage media 612 via the use of interconnect 611 in order to launch, run, execute, interpret or otherwise perform the instructions in fabricator application 140-1 stored on computer readable storage medium 612.

Execution of the fabricator application 140-1 produces processing functionality such as fabricator process 140-2 in processor resource 613. In other words, the fabricator process 140-2 associated with processor resource 613 represents one or more aspects of executing fabricator application 140-1 within or upon the processor resource 613 in the computer system 650.

Those skilled in the art will understand that the computer system 650 can include other processes and/or software and hardware components, such as an operating system that controls allocation and use of hardware resources to execute fabricator application 140-1.

In accordance with different embodiments, note that computer system can be any suitable type of computer device. The computer system 650 may reside at any location or multiple locations in a fabrication environment. As mentioned, the computer system 650 can be included in any suitable resource such as in fabricator resource 151, fabricator resource 152, etc., to implement any functionality as discussed herein.

Figure 7:
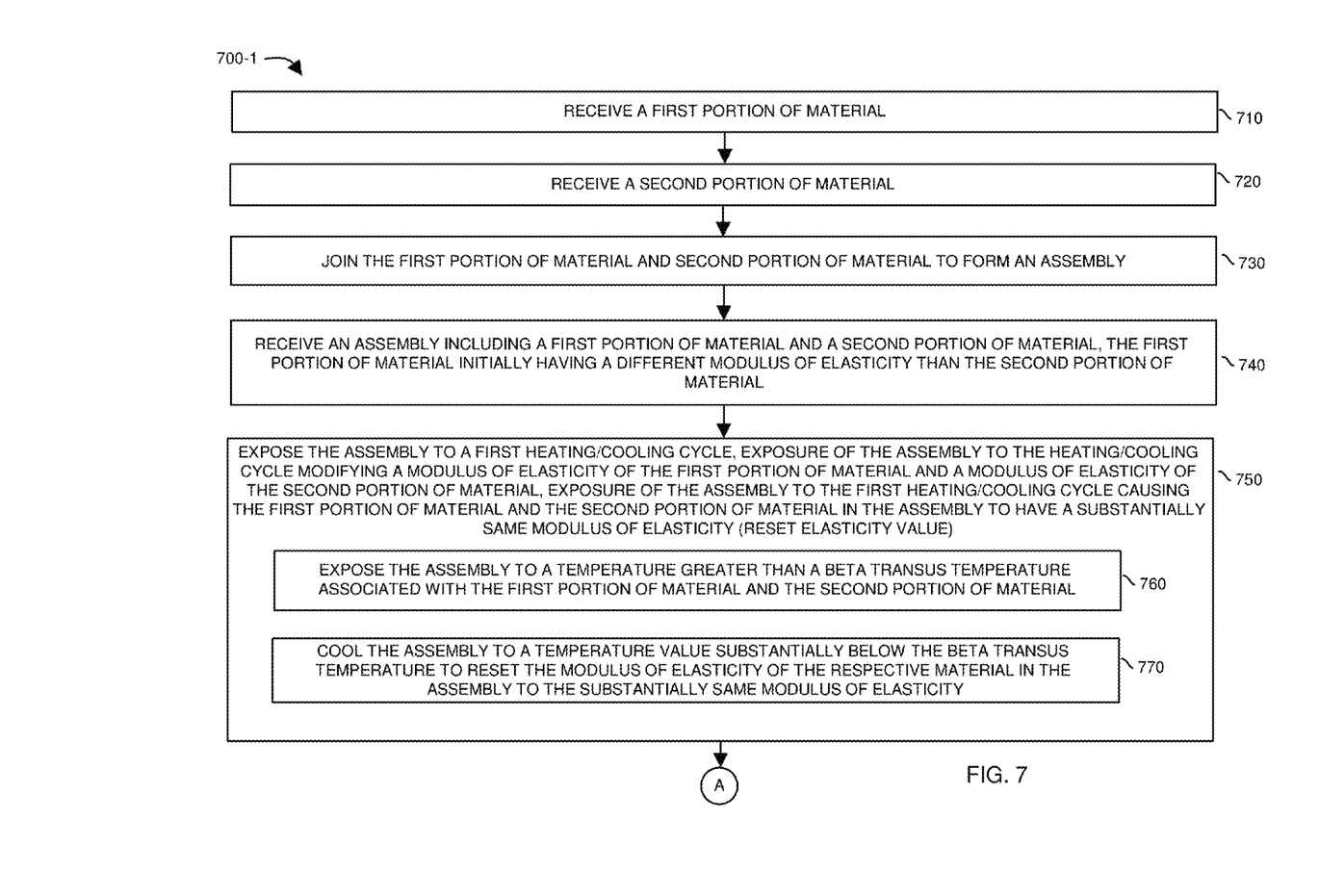
FIGS. 7 and 8 are example diagrams illustrating a method of modifying a modulus of elasticity of material in an assembly according to embodiments herein.

FIG. 7 is a flowchart 700 (flowchart 700-1 and flowchart 700-2) illustrating an example method according to embodiments. Note that there will be some overlap with respect to concepts as discussed above.

In processing block 710, fabricator resource 151 receives a first portion of material 121.

In processing block 720, fabricator resource 151 receives a second portion of material 122.

In processing block 730, fabricator resource 151 produces joint 135 joining the first portion of material 121 and second portion of material 122 to form an assembly 120.

In processing block 740, fabricator resource 152 receives assembly 120 including the first portion of material 121 and a second portion of material 122. In one embodiment, the first portion of material 121 in the assembly 120 initially has a different modulus of elasticity than the second portion of material 122.

In processing block 750, fabricator resource 152 exposes the assembly 120 to a first set of one or more heating/cooling cycles. Exposure of the assembly 120 to the first set of one or more heating/cooling cycles modifies a modulus of elasticity (such as a Young's modulus) of the first portion of material 121 and a modulus of elasticity (such as a Young's modulus) of the second portion of material 122. In one embodiment, exposure of the assembly 120 to the first set of one or more heating/cooling cycles causes the first portion of material 121 and the second portion of material 122 in the assembly 120 to have a substantially same modulus of elasticity (reset elasticity value).

As its name suggests, the first set of one or more heating/cooling cycles includes exposing the assembly 120 to different temperatures. For example, in processing block 760 of processing block 750, fabricator resource 152 exposes the assembly 120 to a temperature greater than a beta transus temperature (such as greater than 985° C.) associated with the first portion of material 121 and the second portion of material 121.

In processing block 770, the fabricator resource 152 quickly cools the assembly 120 to a temperature value substantially below the beta transus temperature (such as back to room temperature) to reset the modulus of elasticity of the respective material in the assembly 120 to the substantially same modulus of elasticity. In one embodiment, as previously discussed, after heating the assembly 120 a sufficiently high temperature (such as above the beta transus temperature), the fabricator resource 152 can be configured to quickly reduce the temperature of the assembly 120 via quench-cooling in which a liquid (such as water, oil, etc., at below 100 degree Celsius) is used to rapidly cool the assembly 120. As discussed above, this resets the modulus of elasticity such as Young's modulus of the material in the assembly 120 to a homogenous value.

Figure 8:
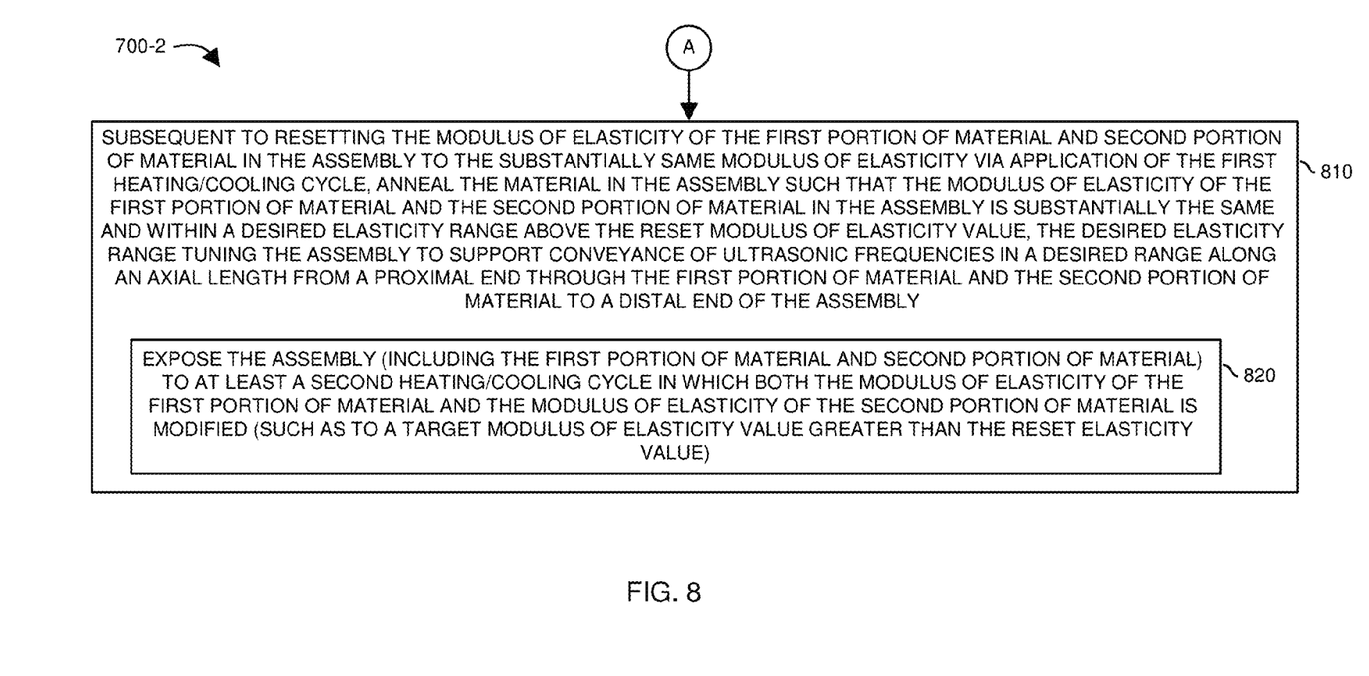

In processing block 810 of FIG. 8, subsequent to resetting the modulus of elasticity of the first portion of material 121 and second portion of material 122 in the assembly 120 to the substantially same modulus of elasticity via application of the first set of one or more heating/cooling cycles, fabricator resource 152 anneals the material in the assembly 120 such that the modulus of elasticity of the first portion of material 121 and the second portion of material 122 in the assembly 120 is substantially the same and within a desired target elasticity range. In one embodiment, the desired target range for the modulus of elasticity is above the reset modulus of elasticity value achieved in processing block 760. Setting the material in assembly 120 to be within a desired elasticity range (such as a Young's modulus value of $E=103.0$ GigaPascals to 110.0 GigaPascals, preferably 104.0 GigaPascals to 109.0 GigaPascals, and most preferably 105.0 GigaPascals to 108.0 Gigapascals.) tunes the assembly 120 to support conveyance of ultrasonic frequencies in a desired range (such as around 50 KiloHertz) along an axial length from a proximal end of assembly 120 through the second portion of material 122 and the first portion of material 121 to a distal end of the assembly 120.

In sub-processing block 820 associated with processing block 810, fabricator resource 152 exposes the assembly 120 (including the first portion of material 121 and second portion of material 122) to at least a second set of one or more heating/cooling cycles in which both the modulus of elasticity of the first portion of material 121 and the modulus of elasticity of the second portion of material 122 is modified (such as to a target modulus of elasticity value greater than the reset elasticity value as set in processing block 750). As previously discussed, the fabricator resource 152 can be configured to expose the assembly 120 to any suitable number of heating/cooling cycles in order to set the material in assembly 120 to an appropriate modulus of elasticity within the desired target range.

Figure 9:
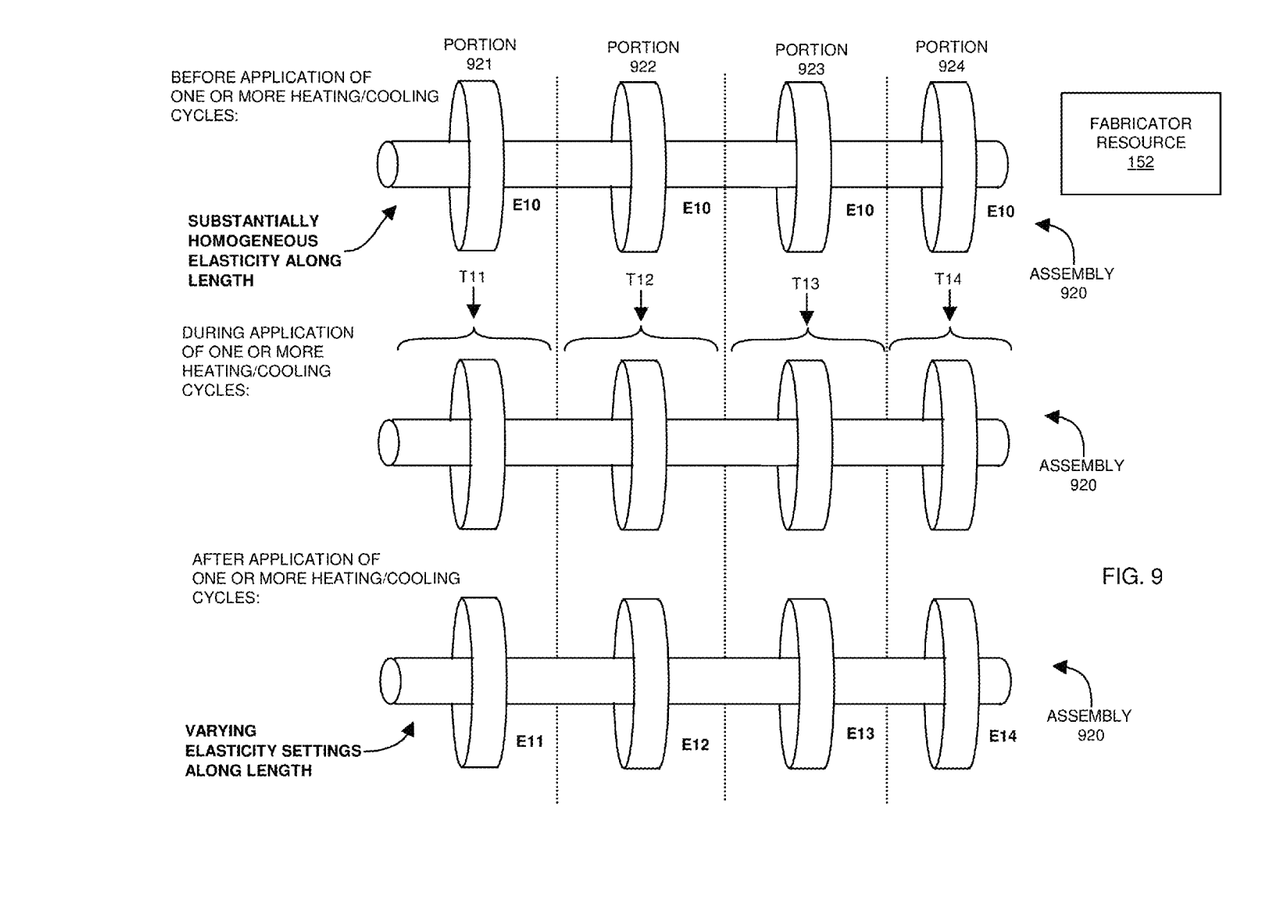
FIG. 9 is an example diagram illustrating exposure of an assembly to one or more different temperatures and/or heating/cooling cycles along a length of an assembly to vary elasticity settings according to embodiments herein.

FIG. 9 is an example diagram illustrating exposure of an assembly to one or more different temperatures along a length to vary elasticity settings (or resonance frequency settings) according to embodiments herein.

Assume in this example embodiment that fabricator resource 152 receives assembly 920 such as a rod of titanium alloy material with respective disks. Note that the shape of assembly 920 as a rod and respective disks is shown by way of non-limiting example. The assembly 920 and corresponding components can be any suitable shape. In this example embodiment, the initial setting of the modulus of elasticity (such as Young's modulus) of material along a length of assembly 920 may be the same (such as E10) or different starting value.

One embodiment herein includes modifying characteristics of assembly 920 such that the modulus of elasticity of different material along the length vary. For example, in one example embodiment, to tune characteristics such as the resonance frequency of the assembly 920 to different values (such as step values, a gradient, etc., along a length of assembly 920), the fabricator resource 152 exposes portion 921 of assembly 920 to one or more temperature heating/cooling cycles as specified by T11; the fabricator resource 152 exposes portion 922 of assembly 920 to one or more temperature heating/cooling cycles as specified by T12; the fabricator resource 152 exposes portion 923 of assembly 920 to one or more temperature heating/cooling cycles as specified by T13; the fabricator resource 152 exposes portion 924 of assembly 920 to one or more temperature heating/cooling cycles as specified by T14.

To obtain different Young's modulus settings, the fabricator resource 152 can be configured to apply different maximum temperatures (for a same or different amount of times) to the different portions 921, 922, etc., of assembly 920.

Exposure of the different portions 921, 922, 923, and 924 to different heating/cooling cycles causes the different portions to be set to different elasticities and, thus, resonance frequency settings. For example, exposure of the portion 921 to a first set of one or more heating/cooling cycles T11 sets the respective Young's modulus of portion 921 to a value of E11 (corresponding to a first resonance frequency value); exposure of the portion 922 to a second set of one or more different heating/cooling cycles T12 sets the respective Young's modulus of portion 922 to a value of E12 (corresponding to a second resonance frequency value); exposure of the portion 923 to a third set of one or more different heating/cooling cycles T13 sets the respective Young's modulus of portion 923 to a value of E13 (corresponding to a third resonance frequency value); exposure of the portion 924 to a fourth set of one or more different heating/cooling cycles T14 sets the respective Young's modulus of portion 924 to a value of E14 (corresponding to a fourth resonance frequency value).

In a manner as previously discussed, if desired, the fabricator resource 152 can be configured to reset the Young's modulus values of the assembly 920 prior to controlling characteristic of the portions in assembly 920 to target elasticity values.

Accordingly, via exposure of different portions of the assembly 920 to different heating/cooling cycle and respective temperatures, the fabricator resource 152: i) tunes the first portion of material 921 to resonate at a first resonant frequency value, ii) tunes the second portion of material 922 resonate at a second resonant frequency value, iii) tunes the third portion of material 923 to resonate at a third resonant frequency value, and iv) tunes the fourth portion of material 924 to resonate at a fourth resonant frequency value. Such an embodiment may be useful in a stirring application in which the disks in assembly 920 are used to agitate one or more liquids at different frequencies.

Figure 10:
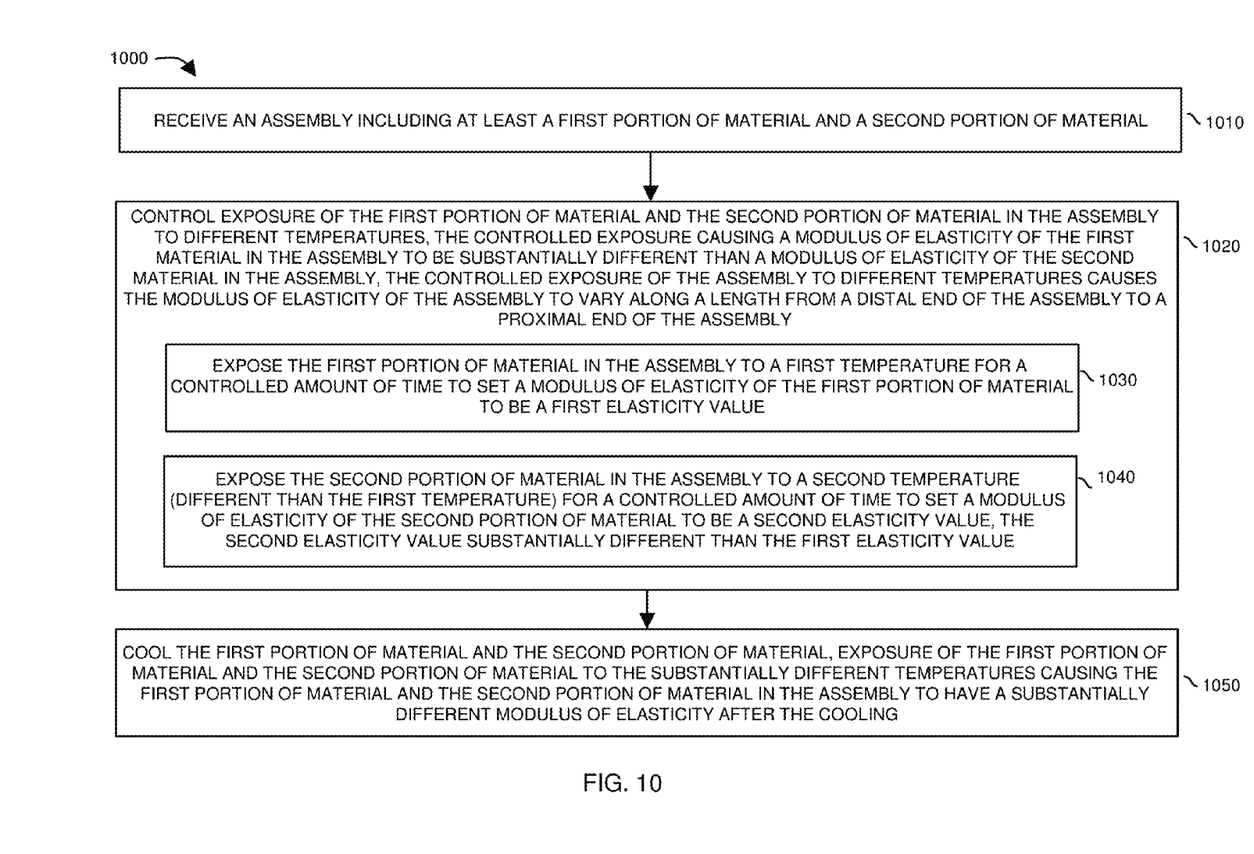
FIG. 10 is an example diagram illustrating a method of setting a modulus of elasticity of material in an assembly to different values according to embodiments herein.

FIG. 10 is a flowchart 1000 illustrating an example method according to embodiments. Note that there will be some overlap with respect to concepts as discussed above.

In processing block 1010, fabricator resource 152 receives an assembly 120 including at least a first portion of material 921 and a second portion of material 922.

In processing block 1020, fabricator resource 152 controls exposure of the first portion of material 921 and the second portion of material 922 in the assembly 920 to different temperatures (e.g., a first location of the assembly 920 along the length is exposed to a first temperature such as T1, a second location of the assembly 920 along the length is exposed to a second temperature T2, etc.). The controlled exposure of different temperatures along the length of assembly 920 causes a modulus of elasticity of the first portion of material 921 (such as at the first location) in the assembly 920 to be substantially different than a modulus of elasticity of the second portion of material 922 (such as at the second location) in the assembly 920. In one embodiment, the controlled exposure of the assembly 920 to different temperatures along the length causes the modulus of elasticity of the assembly 920 to vary along a length from a distal end of the assembly 920 to a proximal end of the assembly 920.

In sub-processing block 1030 of processing block 920, fabricator resource 152 exposes the first portion of material 921 in the assembly 920 to first temperature settings T1 for a controlled amount of time to set a modulus of elasticity of the first portion of material 921 to be a first elasticity value such as E11.

In sub-processing block 1040, fabricator resource 152 exposes the second portion of material in the assembly 920 to second temperature settings T2 (different than the first temperature settings T2) for a controlled amount of time to set a modulus of elasticity of the second portion of material 922 to be a second elasticity value such as E12. In one embodiment, the second elasticity value of the second portion of material 922 is substantially different than the first elasticity value of the first portion of material 921. In this manner, the fabricator resource 152 can control resonant frequency settings of the assembly 920 to different values along its length.

In processing block 1050, fabricator resource 152 cools the assembly 920 including the first portion of material 921 and the second portion of material 922, exposure of the first portion of material 921 and the second portion of material 922 to the substantially different temperature settings (such as T1, T2, T3, etc.) causes the modulus of elasticity to vary along the length of assembly 920 after final cooling. That is, as previously discussed, portion 921 of assembly 920 has a elasticity setting of E11; portion 922 of assembly 920 has an elasticity setting of E12; and so on.

Note again that techniques herein are well suited for modifying elasticity characteristics such as a Young's modulus of material in an assembly. However, it should be noted that embodiments herein are not limited to use in such applications and that the techniques discussed herein are well suited for other applications as well.

While this invention has been particularly shown and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting. Rather, any limitations to the invention are presented in the following claims.

We claim:

1. A method for manufacturing an ultrasonic probe assembly comprising:
   receiving the ultrasonic probe assembly including a first portion of material and a second portion of material, the first portion of material having a different modulus of elasticity than the second portion of material; and
   exposing the ultrasonic probe assembly to a heating/cooling cycle, exposure of the ultrasonic probe assembly to the heating/cooling cycle modifying a modulus of elasticity of the first portion of material and a modulus of elasticity of the second portion of material.

2. The method as in claim 1, wherein exposure of the ultrasonic probe assembly to the heating/cooling cycle causes the first portion of material and the second portion of material in the ultrasonic probe assembly to have a substantially same modulus of elasticity.

3. The method as in claim 2, wherein applying the heating/cooling cycle to the ultrasonic probe assembly includes:
   exposing the ultrasonic probe assembly to a temperature greater than a Beta Transus temperature associated with the first portion of material and the second portion of material; and
   cooling the ultrasonic probe assembly to a temperature value substantially below the Beta Transus temperature to reset the modulus of elasticity of the respective material in the ultrasonic probe assembly to the substantially same modulus of elasticity.

4. The method as in claim 3 further comprising:
   subsequent to resetting the modulus of elasticity of the first portion of material and second portion of material in the ultrasonic probe assembly to the substantially same modulus of elasticity via application of the heating/cooling cycle, annealing the material in the ultrasonic probe assembly such that the modulus of elasticity of the first portion of material and the second portion of material in the ultrasonic probe assembly is substantially the same and within a desired elasticity range above the reset modulus of elasticity value.

5. The method as in claim 4, wherein the desired elasticity range tunes the ultrasonic probe assembly to support conveyance of ultrasonic frequencies in a desired range along an axial length from a proximal end through the first portion of material and the second portion of material to a distal end of the ultrasonic assembly.

6. The method as in claim 1, wherein both the first portion of material and the second portion of material are both Titanium metal alloys.

7. The method as in claim 1, wherein the modulus of elasticity is Young's modulus.

8. The method as in claim 1, wherein the heating cooling cycle is a first heating/cooling cycle in which both the modulus of elasticity of the first portion of material and the modulus of elasticity of the first portion of material and the modulus of elasticity of the second portion of material is reduced to a reset elasticity value, the method further comprising:
   exposing the ultrasonic probe assembly to a second heating/cooling cycle to which both the modulus of elasticity of the first portion of material and the modulus of elasticity of the second portion of material is increased to a target modulus of elasticity value greater than the rest elasticity value.

9. The method as in claim 1, wherein exposing the ultrasonic probe assembly to the heating/cooling cycle includes:
   exposing the first portion of material to a first temperature;
   exposing the second portion of material to a second temperature, the second temperature substantially different than the first temperature; and cooling the first portion of material and the second portion of material, exposure of the first portion of material and the second portion of material to the substantially different temperatures causing the first portion of material and the second portion of material in the ultrasonic probe assembly to have a substantially same modulus of elasticity after the cooling.

* * * * *